United States Patent
Yachida et al.

(10) Patent No.: US 12,243,234 B2
(45) Date of Patent: Mar. 4, 2025

(54) INFORMATION PROCESSING SYSTEM, EYE STATE MEASUREMENT SYSTEM, INFORMATION PROCESSING METHOD, AND NON-TRANSITORY COMPUTER READABLE MEDIUM

(71) Applicants: NEC CORPORATION, Tokyo (JP); THE UNIVERSITY OF TOKYO, Tokyo (JP)

(72) Inventors: Shoji Yachida, Tokyo (JP); Michiaki Inoue, Tokyo (JP); Tomohiro Sueishi, Tokyo (JP)

(73) Assignees: NEC CORPORATION, Tokyo (JP); THE UNIVERSITY OF TOKYO, Tokyo (JP)

( * ) Notice: Subject to any disclaimer, the term of this patent is extended or adjusted under 35 U.S.C. 154(b) by 2 days.

(21) Appl. No.: 18/032,686

(22) PCT Filed: Aug. 11, 2021

(86) PCT No.: PCT/JP2021/029657
§ 371 (c)(1),
(2) Date: Apr. 19, 2023

(87) PCT Pub. No.: WO2022/085276
PCT Pub. Date: Apr. 28, 2022

(65) Prior Publication Data
US 2023/0386038 A1    Nov. 30, 2023

(30) Foreign Application Priority Data
Oct. 20, 2020   (JP) ................................. 2020-176066

(51) Int. Cl.
*H04N 23/695*     (2023.01)
*A61B 3/11*     (2006.01)
(Continued)

(52) U.S. Cl.
CPC ............ *G06T 7/0016* (2013.01); *A61B 3/112* (2013.01); *A61B 3/113* (2013.01); *G06T 7/20* (2013.01);
(Continued)

(58) Field of Classification Search
None
See application file for complete search history.

(56) References Cited

U.S. PATENT DOCUMENTS

| | | | |
|---|---|---|---|
| 2015/0272434 A1* | 10/2015 | Satake | ................. A61B 3/0033 351/206 |
| 2018/0232507 A1 | 8/2018 | Zizi et al. | |

(Continued)

FOREIGN PATENT DOCUMENTS

| | | |
|---|---|---|
| CN | 101059835 A | 10/2007 |
| JP | 10-040386 A | 2/1998 |

(Continued)

OTHER PUBLICATIONS

Craig Hennessey et al., "Long Range Eye Tracking: Bringing Eye Tracking into the Living Room", In Proceedings of the Symposium on Eye Tracking Research and Applications (Santa Barbara, California) (ETRA '12). Association for Computing Machinery, 2012, pp. 249-252.

(Continued)

*Primary Examiner* — Jefferey F Harold
*Assistant Examiner* — Charles N Hicks
(74) *Attorney, Agent, or Firm* — Sughrue Mion, PLLC

(57) ABSTRACT

An information processing system includes a first acquisition unit, a second acquisition unit, a movement control unit, and a state evaluation unit. The first acquisition unit acquires, from a first imaging unit, image data relating to a first image of a head of a subject that is captured at a first angle of view. The second acquisition unit acquires, from a (Continued)

second imaging unit, image data relating to a second image of an eye region of the subject that is captured at a second angle of view narrower than the first angle of view. The movement control unit moves a visual field range of the second imaging unit. The state evaluation unit evaluates a change in state of the eye of the subject.

10 Claims, 11 Drawing Sheets

(51) Int. Cl.
*A61B 3/113* (2006.01)
*G06T 7/00* (2017.01)
*G06T 7/20* (2017.01)
*G06T 7/66* (2017.01)
*G06T 7/70* (2017.01)
*H04N 23/90* (2023.01)

(52) U.S. Cl.
CPC .................. *G06T 7/66* (2017.01); *G06T 7/70* (2017.01); *H04N 23/695* (2023.01); *H04N 23/90* (2023.01); *G06T 2207/30041* (2013.01)

(56) References Cited

U.S. PATENT DOCUMENTS

| | | | |
|---|---|---|---|
| 2018/0360304 A1* | 12/2018 | Kano | A61B 3/0041 |
| 2019/0121105 A1 | 4/2019 | Wang et al. | |
| 2020/0111240 A1* | 4/2020 | Gupta | G06T 11/00 |
| 2020/0326773 A1 | 10/2020 | Bigioi et al. | |

FOREIGN PATENT DOCUMENTS

| | | |
|---|---|---|
| JP | 2005-323905 A | 11/2005 |
| JP | 2016-220801 A | 12/2016 |
| JP | 2018-088647 A | 6/2018 |
| JP | 2018-103745 A | 7/2018 |
| JP | 2019-195377 A | 11/2019 |
| WO | 2012/001755 A1 | 1/2012 |
| WO | 2016/195066 A1 | 12/2016 |
| WO | 2020/188629 A1 | 9/2020 |

OTHER PUBLICATIONS

Dong-Chan Cho et al., "Long-Range Gaze Tracking System for Large Movements", IEEE Transactions on Biomedical Engineering, Dec. 2013, vol. 60, No. 12, pp. 3432-3440.

International Search Report for PCT/JP2021/029657 dated Sep. 28, 2021.

Extended European Search Report dated Jul. 30, 2024 from the European Patent Office in Application No. 21882417.5.

Supratim Gupta et al., "Estimation of Saccadic Ratio from Eye Image Sequences to Detect Human Alertness", IEEE Proceedings of 4th International Conference on Intelligent Human Computer Interaction, Dec. 27-29, 2012, 6 pages total.

Communication dated Oct. 8, 2024 from the Japanese Patent Office in Application No. 2022-556425.

* cited by examiner

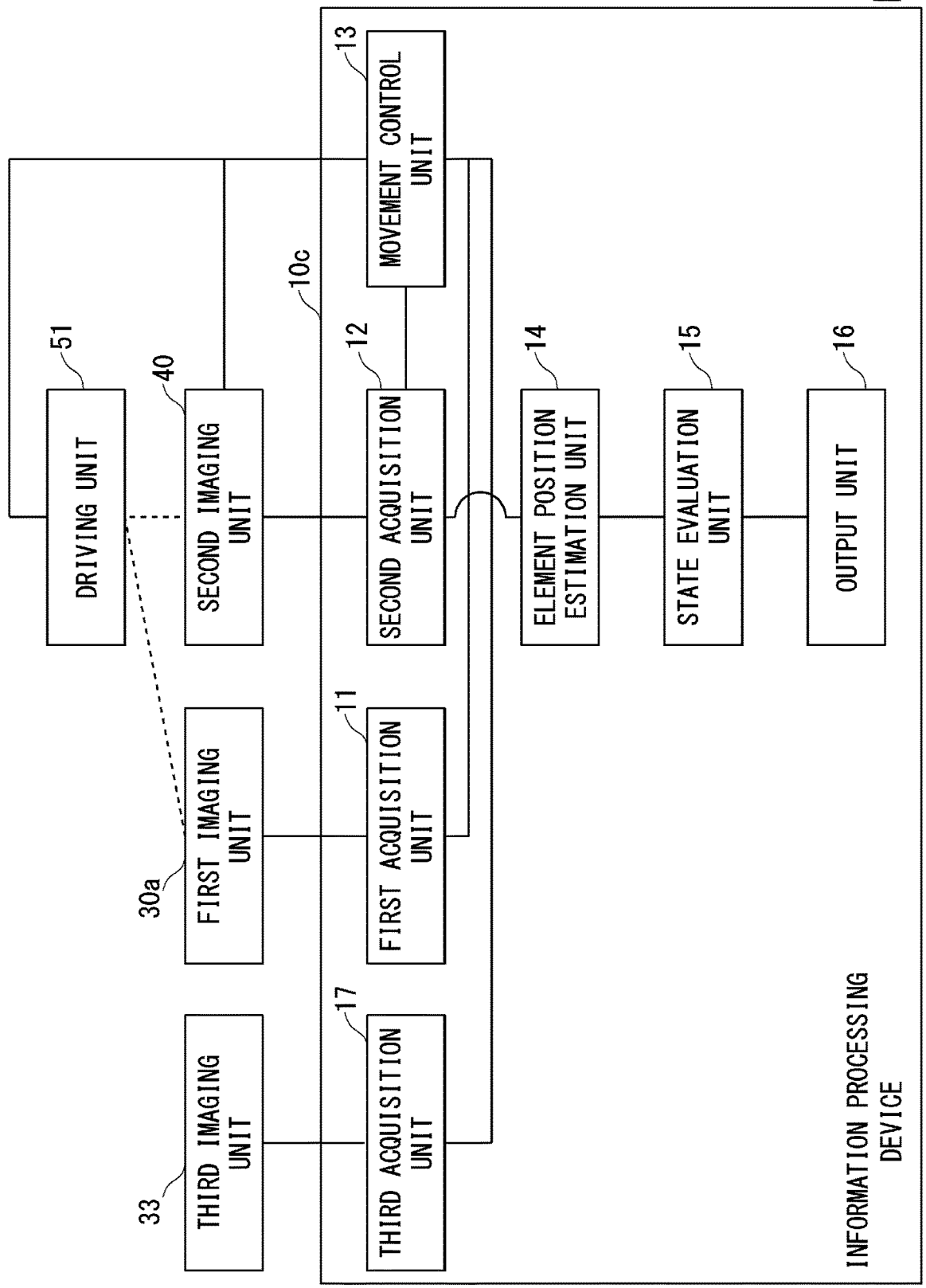

INFORMATION PROCESSING SYSTEM, EYE STATE MEASUREMENT SYSTEM, INFORMATION PROCESSING METHOD, AND NON-TRANSITORY COMPUTER READABLE MEDIUM

This Application is a National Stage of International Application No. PCT/JP2021/029657 filed Aug. 11, 2021, claiming priority based on Japanese Patent Application No. 2020-176066 filed Oct. 20, 2020.

TECHNICAL FIELD

The present disclosure relates to an information processing system, an eye state measurement system, an information processing method, and a non-transitory computer readable medium, more particularly to an information processing system, an eye state measurement system, an information processing method, and a non-transitory computer readable medium that evaluate a change in state of an eye of a subject.

BACKGROUND ART

There has been proposed a technique of evaluating a change in state of an eye of a subject, based on a captured image of the eye of the subject. For example, Patent Literature 1 discloses a method of calculating a pupil motion from a change in a pupil position detected based on a captured image of a face of a driver. However, in the above-mentioned method described in Patent Literature 1, when a head moves and an eyeball is not within a visual field range of a camera, a pupil position cannot be detected. Therefore, the subject is required to fix the head in such a way that the eyeball stays within the visual field range of the camera.

Further, Patent Literature 2 discloses a method of detecting a movement amount of an eyeball, based on a difference between a reference position indicating a position of a blood vessel figure in a white region of an eye in a reference image and a position of the blood vessel figure in the white region of the eye in an image for detection. In this method, an eyeball image in the image for detection is corrected to be at a position in the reference image through Affine conversion from three positions including positions of an inner eye corner and an outer eye corner, and hence image blurring can be prevented. However, even in this method, a subject is also required to fix the head to a certain extent in such a way that the eyeball stays within a visual field range of a camera.

Meanwhile, there has been known a method of capturing an image of a designated region in an enlarged manner through use of cameras with different angles of view. Patent Literature 3 discloses an information processing system in which a second narrow-angle camera captures an image of a target region designated in an image captured by a first wide-angle camera. However, the second camera is limited for capturing an image of a human face, and Patent Literature 3 described above does not disclose capturing an image of an eye region being a micro region. Further, Patent Literature 3 described above does not disclose a technique of measuring and evaluating a microscopic change in state of an eye.

CITATION LIST

Patent Literature

[Patent Literature 1]
   Japanese Unexamined Patent Application Publication No. 2019-195377
[Patent Literature 2]
   International Patent Publication No. WO2016/195066
[Patent Literature 3]
   International Patent Publication No. WO2012/001755

SUMMARY OF INVENTION

Technical Problem

The present disclosure has been made in order to solve the problems described above, and an object thereof is to provide an information processing system, an eye state measurement system, an information processing method, and a non-transitory computer readable medium that suitably evaluate a change in state of an eye of a subject while a head is in a relaxed posture without being fixed.

Solution to Problem

An information processing system according to one aspect of the present disclosure includes a first acquisition means, a second acquisition means, a movement control means, and a state evaluation means. The first acquisition means acquires, from a first imaging means, image data relating to a first image of a head of a subject, the first image being captured at a first angle of view. The second acquisition means acquires, from a second imaging means, image data relating to a second image of an eye region of the subject, the second image being captured at a second angle of view narrower than the first angle of view. The movement control means moves a visual field range of the second imaging means, based on position information relating to the head of the subject, the position information being acquired based on the first image. The state evaluation means evaluates a change in state of an eye of the subject, based on chronological data relating to the second image.

An eye state measurement system according to one aspect of the present disclosure includes a first imaging means, a second imaging means, and an information processing device. The first imaging means captures an image of a head of a subject at a first angle of view. The second imaging means captures an image of an eye region of the subject at a second angle of view narrower than the first angle of view. The information processing device includes a first acquisition means, a second acquisition means, a movement control means, and a state evaluation means. The first acquisition means acquires, from a first imaging means, image data relating to a first image of a head of a subject, the first image being captured at a first angle of view. The second acquisition means acquires, from a second imaging means, image data relating to a second image of an eye region of the subject, the second image being captured at a second angle of view narrower than the first angle of view. The movement control means moves a visual field range of the second imaging means, based on position information relating to the head of the subject, the position information being acquired based on the first image. The state evaluation means evaluates a change in state of an eye of the subject, based on chronological data relating to the second image.

An information processing method according to one aspect of the present disclosure includes: acquiring, from a first imaging means, image data relating to a first image of a head of a subject, the first image being captured at a first angle of view; acquiring, from a second imaging means, image data relating to a second image of an eye region of the subject, the second image being captured at a second angle of view narrower than the first angle of view; moving a visual field range of the second imaging means, based on position information relating to the head of the subject, the position information being acquired based on the first image; and evaluating a change in state of an eye of the subject, based on chronological data relating to the second image.

A non-transitory computer readable medium according to one aspect of the present disclosure stores a program for causing a computer to execute first acquisition processing, second acquisition processing, movement control processing, and state evaluation processing. The first acquisition processing is processing of acquiring, from a first imaging means, image data relating to a first image of a head of a subject, the first image being captured at a first angle of view. The second acquisition processing is processing of acquiring, from a second imaging means, image data relating to a second image of an eye region of the subject, the second image being captured at a second angle of view narrower than the first angle of view. The movement control processing is processing of moving a visual field range of the second imaging means, based on position information relating to the head of the subject, the position information being acquired based on the first image. The state evaluation processing is processing of evaluating a change in state of an eye of the subject, based on chronological data relating to the second image.

Advantageous Effects of Invention

According to the present disclosure, it is possible to provide an information processing system, an eye state measurement system, an information processing method, and a non-transitory computer readable medium that suitably evaluate a change in state of an eye of a subject while a head is in a relaxed posture without being fixed.

BRIEF DESCRIPTION OF DRAWINGS

FIG. 11 is a block diagram illustrating a functional configuration of an information processing device according to the fourth example embodiment.

EXAMPLE EMBODIMENT

The present disclosure is described below based on example embodiments, but the invention within the scope of the claims is not limited to the embodiments given below. Further, not all the configurations described in the example embodiments are necessary as means for solving the problems. For clarification of the description, the description and the drawings given below are omitted and simplified as appropriate. Note that, in each of the drawings, the same elements are denoted with the same reference symbols.

First Example Embodiment

Figure 1:
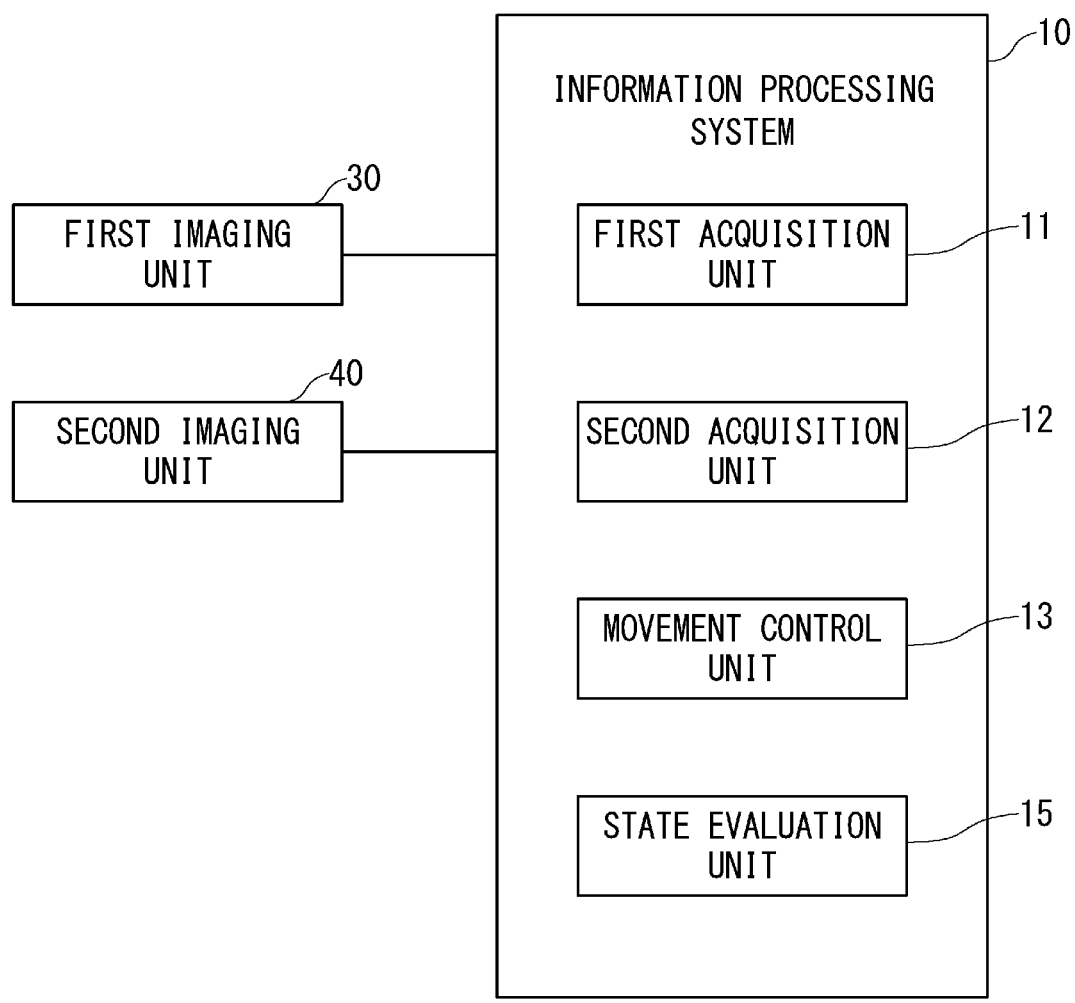
FIG. 1 is a block diagram illustrating a functional configuration of an information processing system according to a first example embodiment.
Figure 2:
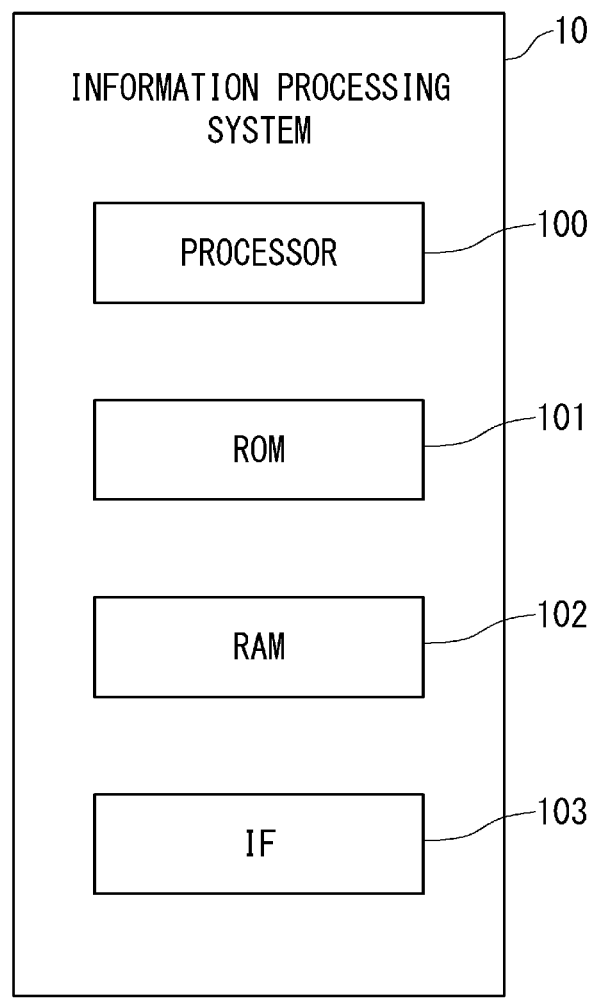
FIG. 2 is a block diagram illustrating a hardware configuration of the information processing system according to the first example embodiment.

First, with reference to FIG. 1 and FIG. 2, a first example embodiment of the present disclosure is described. FIG. 1 is a block diagram illustrating a functional configuration of an information processing system 10 according to the first example embodiment. The information processing system 10 is a computer device that evaluates a change in state of an eye of a subject. The information processing system 10 includes a first acquisition unit 11, a second acquisition unit 12, a movement control unit 13, and a state evaluation unit 15.

The first acquisition unit 11 is also referred to as a first acquisition means. The first acquisition unit 11 is connected to a first imaging unit 30 in a communicable manner, and acquires, from the first imaging unit 30, image data (first image data) relating to a first image of a head of subject that is captured at a first angle of view. Herein, the first imaging unit 30 is a camera that captures an image of the head of the subject at the first angle of view. The first imaging unit is also referred to as a first imaging means.

The second acquisition unit 12 is also referred to as a second acquisition means. The second acquisition unit 12 is connected to a second imaging unit 40 in a communicable manner, and acquires, from the second imaging unit 40, image data (second image data) relating to a second image of an eye region of the subject that is captured at a second angle of view. Herein, the second imaging unit 40 is a camera that captures an image of the eye region of the subject at the second angle of view. The second imaging unit 40 is also referred to as a second imaging means. The second angle of view is narrower than the first angle of view. Further, the eye region may be an eyeball or a peripheral region including an eyeball.

The movement control unit 13 is also referred to as a movement control means. The movement control unit 13 moves a visual field range of the second imaging unit 40, based on position information relating to the head of the subject that is acquired based on the first image. The visual field range of the second imaging unit 40 is a range that is captured as an image by the second imaging unit and is also referred to as a capture volume. The visual field range is defined based on an angle of view and a camera optical axis, and is wider as the angle of view is larger.

The state evaluation unit 15 is also referred to as a state evaluation means. The state evaluation unit 15 evaluates a change in state of the eye of the subject, based on chronological data relating to the second image.

FIG. 2 is a block diagram illustrating a hardware configuration of the information processing system 10 according to the first example embodiment.

The information processing system 10 includes a processor 100, a read only memory (ROM) 101, a random access memory (RAM) 102, and an interface (IF) unit 103 as main hardware configurations. The processor 100, the ROM 101, the RAM 102, and the interface unit 103 are connected mutually to one another via a data bus or the like.

The processor 100 has a function as an arithmetic device that executes control processing and arithmetic processing. The processor 100 may be a central processing unit (CPU), a graphics processing unit (GPU), a field-programmable gate array (FPGA), a digital signal processor (DSP), an application specific integrated circuit (ASIC), or a combination thereof. The ROM 101 has a function of storing a control program, an arithmetic program, and the like that are executed by the processor 100. The RAM 102 has a function of temporarily storing processing data and the like. The interface unit 103 performs input and output of a signal with the outside in a wired or wireless manner. Further, the interface unit 103 receives an input operation of data from a user, and displays information for the user. For example, the interface unit 103 communicates with the first imaging unit 30 and the second imaging unit 40.

As described above, with the information processing system 10 according to the first example embodiment, the visual field range of the narrow-angle camera is moved based on the position information relating to the head of the subject that is acquired based on the first wide-angle image, the eye region is captured as an enlarged image, and thus a change in state of the eye is evaluated. Therefore, even when the head of the subject is not fixed, the eye region can be prevented from deviating from the visual field range of the narrow-angle camera. With this, the information processing system 10 can suitably evaluate a change in state of the eye of the subject while the head is in a relaxed posture without being fixed.

Second Example Embodiment

Figure 3:
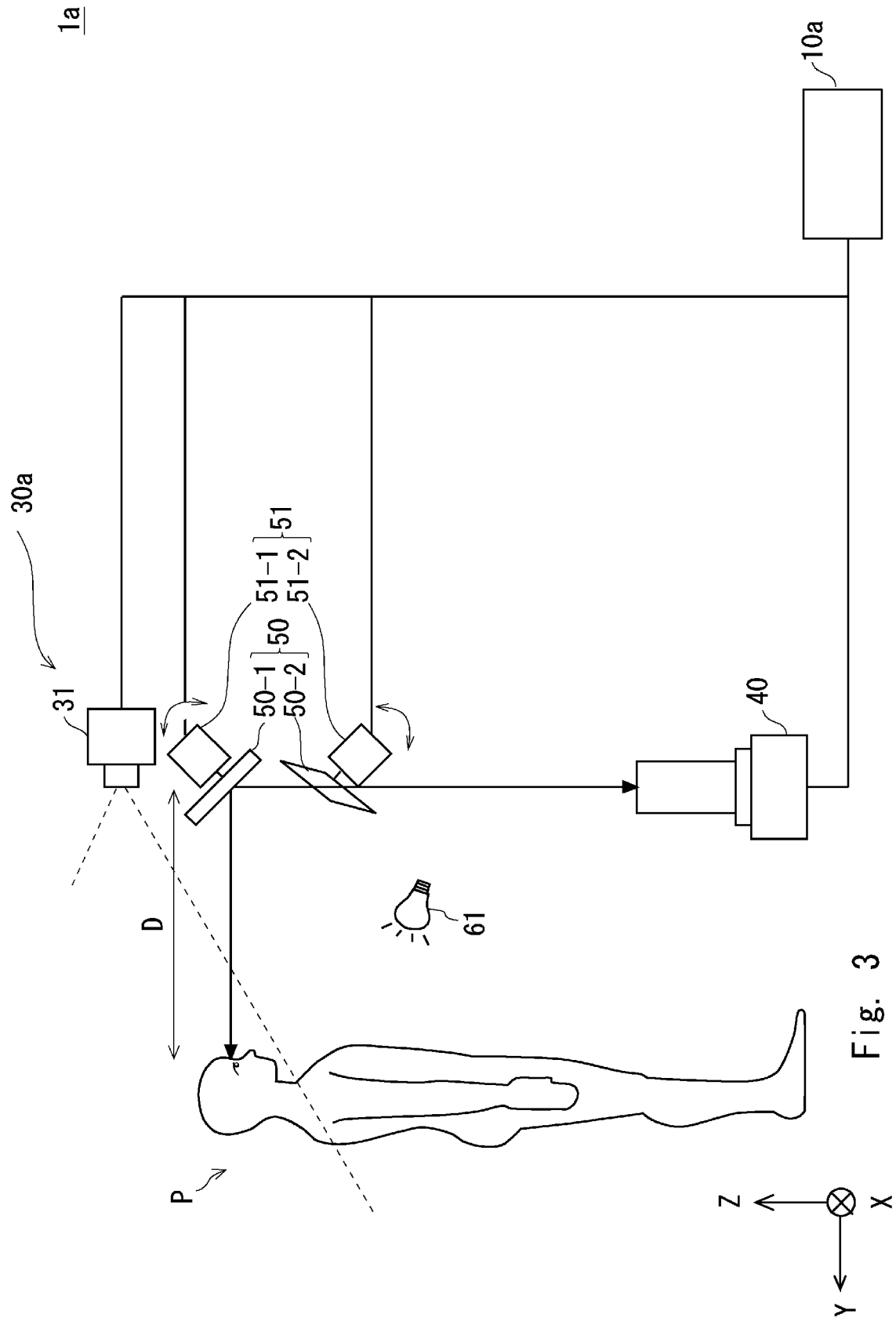
FIG. 3 is a system configuration diagram of an eye state measurement system to which an information processing system according to a second example embodiment is applicable.

FIG. 3 is a system configuration diagram of an eye state measurement system 1a to which an information processing system (hereinafter, referred to as an information processing device) according to a second example embodiment is applicable. Note that, in this drawing, it is assumed that a right-and-left direction of a subject P corresponds to an X-axis direction, a front-and-rear direction of the subject P corresponds to a Y-axis direction, and an up-and-down direction of the subject P corresponds to the Z-axis direction.

Herein, the eye state measurement system 1a is a computer system that measures and evaluates a change in state of the eye of the subject. In the second example embodiment, the eye state measurement system 1a measures and evaluates a vibration state of a pupil that is caused by a saccade phenomenon. The eye state measurement system 1a includes an information processing device a first imaging unit 30a, the second imaging unit 40, and a movable mirror a driving unit 51, and a light source 61. Note that a distance between the first imaging unit 30a and the subject P in the Y-axis direction is denoted as D. D is, for example, 2±0.5 [m].

The information processing device 10a is associated with the information processing system 10 in FIG. 1. The information processing device 10a is connected to the first imaging unit 30a, the second imaging unit 40, and the driving unit 51. When the first image data is received from the first imaging unit 30a, the information processing device 10a generates a control signal required for causing the eye region of the subject P to fall within the visual field range of the second imaging unit 40 and a control signal required for causing the second imaging unit 40 to focus on the eye region of the subject P. Then, the information processing device 10a transmits the control signal for the visual field range in the X-axis direction and the Z-axis direction to the driving unit 51, and transmits the control signal for the focal position to the second imaging unit 40.

The first imaging unit 30a is a camera having a function similar to that of the first imaging unit 30 in FIG. 1. In the second example embodiment, the first imaging unit 30a includes a wide-angle camera 31. The wide-angle camera 31 captures an image of at least a face of the subject P, and generates the first image data. A focal distance of the wide-angle camera 31 is set in advance in such a way that the face of the subject P at a distance of D [m] can be captured as an image. For example, the focal distance of the wide-angle camera 31 may be less than 200 [mm], preferably less than 70 [mm], and is 28 [mm] in the second example embodiment. Note that the focal distance of the wide-angle camera 31 may be 12 [mm].

A frame rate of the wide-angle camera 31 is set in advance in such a way as to follow vibration of the eye region due to vibration of the head of the subject P and suppress an excessive increase of the data amount. For example, the frame rate of the wide-angle camera 31 may be 120 [fps] to 1,200 [fps], preferably 240 [fps] to 1,000 [fps], more preferably 480 [fps] to 1,000 [fps], and is 500 [fps] in the second example embodiment. Herein, the wide-angle camera 31 may capture an image of an object at a frame rate equal to or greater than a frame rate of the second imaging unit 40 described later. With this, the visual field range of the second imaging unit 40 can easily be controlled in a suitable manner, according to vibration of the eye region.

When the first image data is generated, the wide-angle camera 31 transmits the first image data to the information processing device 10a.

The second imaging unit 40 is a camera that captures an image of the eye region of the subject at the second angle of view narrower than the first angle of view and generates the second image data. For facilitation of pupil detection described later, the second imaging unit 40 may be a near-infrared ray camera. A detection wavelength of a photodetector of the second imaging unit 40 is referred to as a wavelength for pupil detection, and the wavelength for pupil detection is a wavelength of, for example, 940 [nm]. Further, the second imaging unit 40 includes a telephoto lens and a liquid lens. The liquid lens is a lens for determining a focal position (focus point), and may be controlled based on the control signal for the focal position from the information processing device 10a. The focal distance of the second imaging unit 40 is set in such a way as to capture an image of the eye region of the subject P at the distance D [m] from the movable mirror 50, and is longer than the focal distance of the wide-angle camera 31. For example, the focal distance of the second imaging unit 40 may be 100 [mm] or longer, preferably 150 [mm] or longer, and is 200±50 [mm] in the second example embodiment. Herein, the second imaging unit 40 has a long focal distance, and thus has an extremely narrow depth of field. Therefore, the second imaging unit 40 controls the focal position, based on the distance information, and thus focuses on the eye region (focusing). Further, the frame rate of the second imaging unit 40 is set in advance in such a way as to observe a change in state of the eye, in this example, a saccade phenomenon, and suppress an excessive increase of the data amount. For example, the frame rate of the second imaging unit 40 may be 120 [fps] to 1,000 [fps], preferably 240 [fps] to 1,000 [fps], more preferably 500 [fps] to 1,000 [fps], and is 500 [fps] in the second example embodiment. When the second image data is generated, the second imaging unit 40 transmits the second image data to the information processing device 10a.

The movable mirror 50 is a pair of mirrors that move an optical axis of the second imaging unit 40. The movable mirror 50 includes a first movable mirror 50-1 and a second movable mirror 50-2. In the following description, when there is no need to discriminate the first movable mirror 50-1 and the second movable mirror 50-2 from each other, the movable mirror 50 is simply used. Each of the movable mirrors 50 is connected to the driving unit 51 via a support portion (not illustrated) in a fixed manner in such a way as to form a predetermined inclination angle, and is configured in such a way as to change the inclination angle along with rotation of the support portion. For example, the first movable mirror 50-1 is configured in such a way that the support portion being the connection destination rotates about the Z-axis, and the second movable mirror 50-2 is configured in such a way that the support portion being the connection destination rotates about the X-axis. With this, the movable mirror is capable of moving the optical axis of the second imaging unit 40 in the X-axis direction and the Z-axis direction, that is, moving the visual field range of the second imaging unit 40 in the X-axis direction and the Z-axis direction.

Note that, in the first example embodiment, the movable mirror 50 is a galvanometer mirror having a relatively small mass and high responsiveness. With this, the eye state measurement system 1a easily captures an image of the eye region while associating the visual field range of the second imaging unit 40 with microscopic and high-speed movement of the head of the subject P.

The driving unit 51 is also referred to as a driving means. The driving unit 51 is a driving motor that rotates each of the movable mirrors 50 via the support portion. The driving unit 51 includes a first driving unit 51-1 associated with the first movable mirror 50-1 and a second driving unit 51-2 associated with the second movable mirror 50-2. Note that the first driving unit 51-1 and the second driving unit 51-2 are also simply referred to as the driving unit 51. Herein, the driving unit 51 rotates the movable mirror 50, based on the control signal for the visual field range in the X-axis direction and the Z-axis direction from the information processing device 10a.

The light source 61 is a light source that irradiates the face of the subject P. The light source 61 is a light source having a wavelength region associated with the wavelength for pupil detection, and is a near-infrared light source of 940 [nm] in the second example embodiment.

In other words, the second imaging unit 40 captures an image of the eye region of the subject P with incident light through a path including the eye region of the subject P, the first movable mirror 50-1, the second movable mirror 50-2, and the second imaging unit 40 in the stated order.

Figure 4:
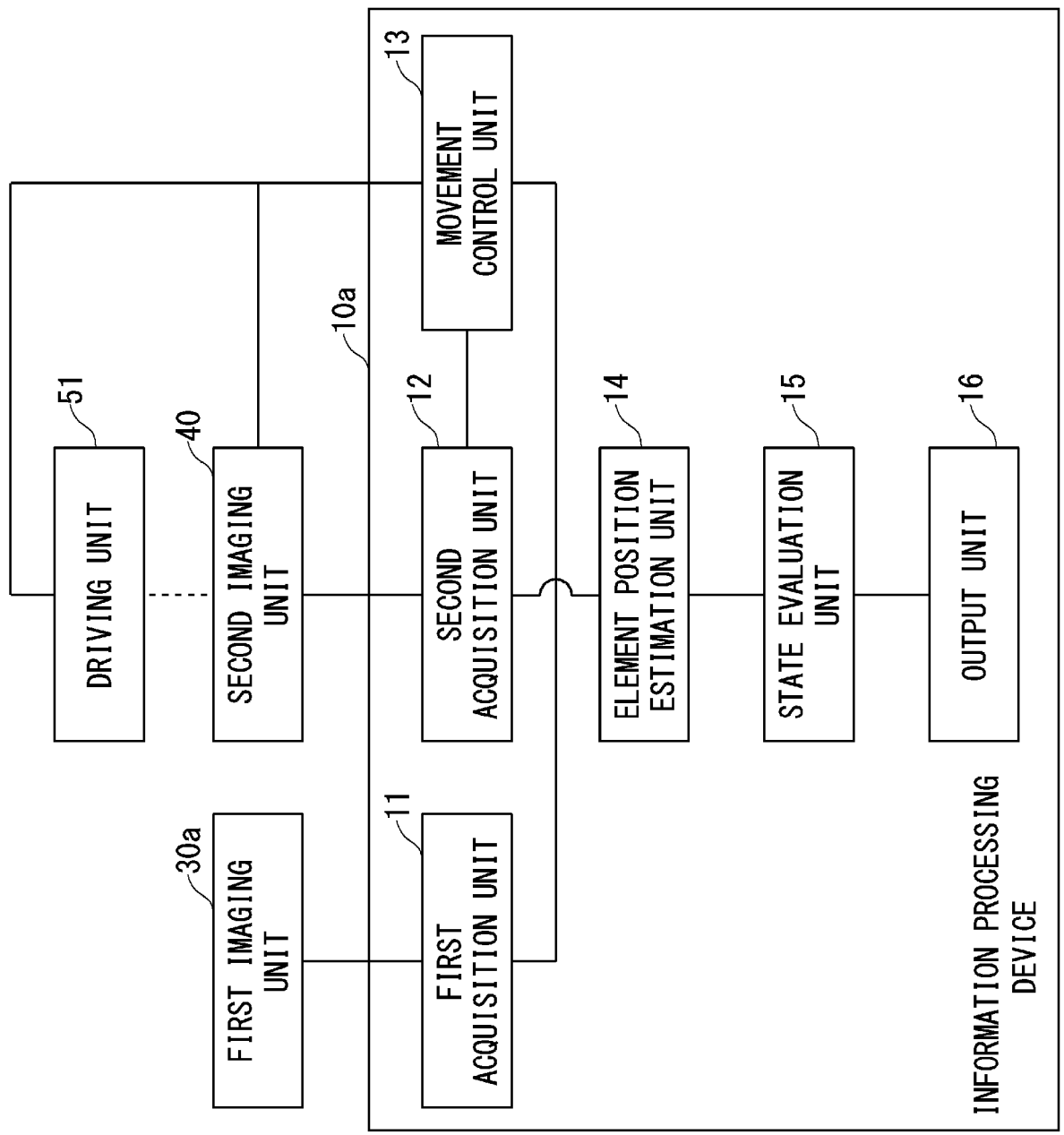
FIG. 4 is a block diagram illustrating a functional configuration of an information processing device according to the second example embodiment.

FIG. 4 is a block diagram illustrating a functional configuration of the information processing device 10a according to the second example embodiment. The information processing device 10a in FIG. 4 includes an element position estimation unit 14 and an output unit 16 in addition to the configuration elements of the information processing device 10 in FIG. 1.

The first acquisition unit 11 is connected to the first imaging unit 30a (the wide-angle camera 31), and receives and acquires the first image data from the first imaging unit 30a. The first acquisition unit 11 may acquire the first image data at the frame rate equal to or greater than the frame rate at which the second acquisition unit 12 acquires the second image data. The first acquisition unit 11 supplies the first image data thus acquired to the movement control unit 13.

The second acquisition unit 12 is connected to the second imaging unit 40, and receives and acquires the second image data from the second imaging unit 40. The second acquisition unit 12 supplies the second image data thus acquired to the element position estimation unit 14. Further, the second acquisition unit 12 may supply the second image data thus acquired to the movement control unit 13.

The movement control unit 13 generates change information relating to a position of the face of the subject P in the X-axis direction and the Z-axis direction, based on chronological data relating to the first image. The movement control unit 13 calculates each of rotation amounts of the first movable mirror 50-1 and the second movable mirror 50-2, based on the change information. The movement control unit 13 may use the second image data in addition to the change information for calculating the rotation amounts. Then, the movement control unit 13 generates the control signal for the visual field range in the X-axis direction and the Z-axis direction, based on each of the rotation amounts, transmits the control signal for the visual field range in the Z-axis direction to the first driving unit 51-1, and transmits the control signal for the visual field range in the X-axis direction to the second driving unit 51-2. Further, the movement control unit 13 executes focal position control processing, based on the chronological data relating to the first image and the second image, generates the change information relating to a position of the face of the subject P in the Y-axis direction, and generates the control signal for the focal position. Further, the movement control unit 13 transmits the control signal to the second imaging unit 40, to control the liquid lens. In this manner, the second imaging unit 40 moves the visual field range and the focal position (focus point), based on the change information relating to the position of the face.

The element position estimation unit 14 is also referred to as an element position estimation means. The element position estimation unit 14 estimates a position of an element of an eye in the second image. In the second example embodiment, the position of the element of the eye that is estimated by the element position estimation unit 14 includes a gravity center position of the pupil of the subject P and positions of an outer eye corner and an inner eye corner. Note that any one of the positions of the outer eye corner and the inner eye corner may be used, or a position of another freely selected point may be used instead. The element position estimation unit 14 supplies the position information relating to the element of the eye to the state evaluation unit 15.

The state evaluation unit 15 generates difference information relating to the position of the element of the eye in the second image, and evaluates the vibration state of the pupil of the subject P, based on the difference information.

The vibration state of the pupil may be at least one of a vibration amount, a vibration direction, a vibration frequency, and a vibration duration of the pupil. The state evaluation unit 15 supplies the information relating to the vibration state of the pupil to the output unit 16.

The output unit 16 is also referred to as an output means. The output unit 16 outputs the information relating to the vibration state of the pupil, as an evaluation result. The output unit 16 may include a display unit (not illustrated) that displays the evaluation result. Further, the output unit 16 may include a transmission unit (not illustrated) that transmits the evaluation result to an external device (not illustrated).

Figure 5:
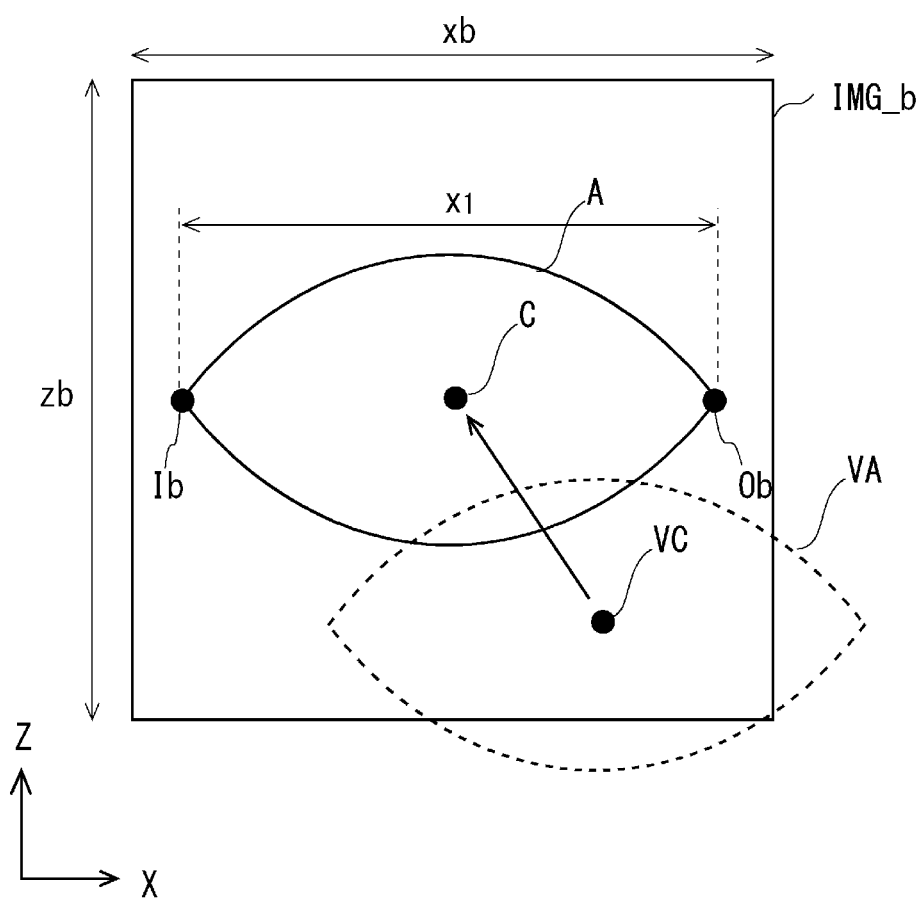
FIG. 5 is a diagram for describing movement control processing executed by a movement control unit according to the second example embodiment.

Herein, with reference to FIG. 5, movement control processing is described in detail. FIG. 5 is a diagram for describing the movement control processing executed by the movement control unit 13 according to the second example embodiment. In this drawing, a second image IMG_b is illustrated. An eye region including an inner eye corner Ib and an outer eye corner Ob of the subject P is captured as the second image IMG_b.

First, the movement control unit 13 calculates position coordinates of the eye region in the first image (referred to as eye position coordinates). In the second example embodiment, the eye position coordinates are, but not limited to, position coordinates of the gravity center of the eye region when the eye region in the first image is similar to a substantially elliptic region, and may be a position coordinate range of the eye region in the first image. Subsequently, the movement control unit 13 calculates position coordinates of a gravity center VC of an image region (projection region) VA in the second image, the position coordinates being associated with the eye position coordinates in the first image when the eye region in the first image is virtually projected onto the second image IMG_b. In this case, the movement control unit 13 may calculate the position coordinates of the gravity center VC of the projection region VA, based on the difference information relating to the eye position coordinates in the first image between the previous image-capturing timing and the current image-capturing timing and the second image at the previous image-capturing timing. Note that the difference information relating to the eye position coordinates is an example of the change information relating to the position of the face that is described above. Then, the movement control unit 13 calculates the rotation amounts of the first movable mirror 50-1 and the second movable mirror 50-2 in such a way that the gravity center VC of the projection region VA is arranged at the center C of the second image. With this, the movement control unit 13 is capable of moving the visual field range of the second imaging unit 40 in the X-axis direction and the Z-axis direction in such a way that an eye region A is always arranged at the center of the second image IMG_b. Note that, in this drawing, the projection region VA and the eye region A are substantially elliptic regions that are symmetric with respect to the major axis and the minor axis, and an intermediate point between the outer eye corner Ob and the inner eye corner Ib that are positioned on both ends of each of the projection region VA and the eye region A matches with the gravity center.

Note that the number of pixels in the width direction of the eye region included in the second image IMG_b is set in such a way as to fall within a predetermined range with respect to the number of pixels in the width direction of the second image IMG_b. The number of pixels in the width direction of the second image IMG_b is denoted with xb, and the number of pixels in the height direction is denoted with zb. As an example, xb×zb=640×480 is satisfied. Further, the number of pixels from the inner eye corner Ib to the outer eye corner Ob of the subject P captured in the second image IMG_b is denoted with x1. In other words, x1/xb is maintained to fall within a predetermined range. For example, x1/xb is 0.5 or greater and less than 1, preferably 0.8 or greater and less than 1. With this, the information processing device 10a is capable of detecting a pupil from the second image IMG_b at high accuracy.

Herein, when the movement control unit 13 controls movement of the first movable mirror 50-1 and the second movable mirror 50-2 in such a way that the eye region A is arranged at the center of the second image IMG_b, the rotation amounts differ according to the distance D between the camera and the subject P in the Y-axis direction. Therefore, the movement control unit 13 is required to adjust the focus of the second image IMG_b.

Figure 6:
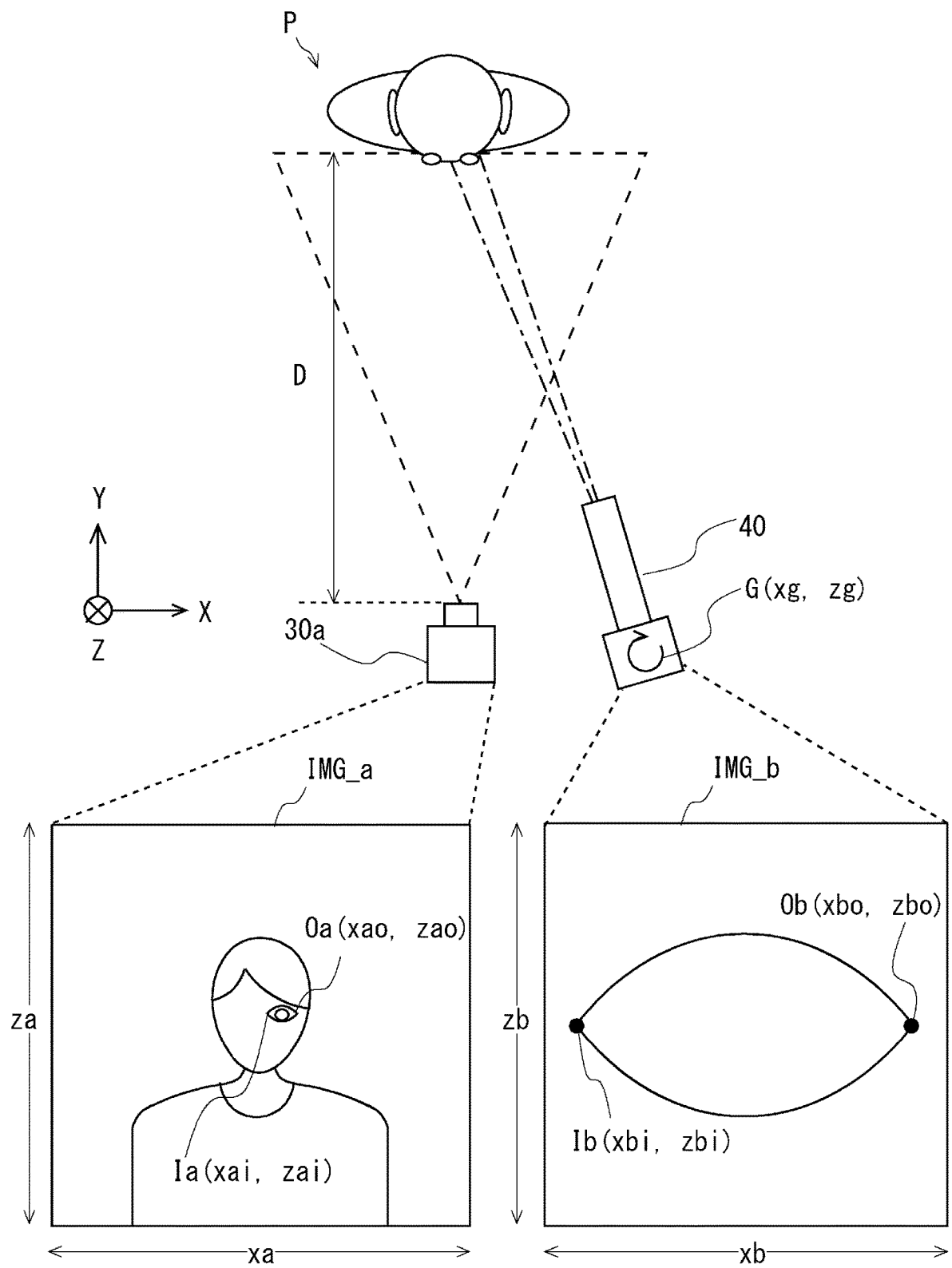
FIG. 6 is a diagram for describing focal position control processing executed by the movement control unit according to the second example embodiment.

Herein, FIG. 6 is a diagram for describing the focal position control processing executed by the movement control unit 13 according to the second example embodiment. This drawing illustrates a top schematic diagram the subject P, the first imaging unit 30a, and the second imaging unit 40 in the upper part, and illustrates the first imageIMG_a of the first imaging unit 30a and the second image IMG_b of the second imaging unit 40 in the lower part.

First, the movement control unit 13 calculates position coordinates (xai, zai) of an inner eye corner Ia of the subject P in the first image IMG_a. Then, the movement control unit 13 controls rotation of the movable mirror 50 to acquire the second image IMG_b. At this state, an angle of the movable mirror is denoted with G (xg, zg). The movement control unit 13 calculates position coordinates (xbi, zbi) of the inner eye corner Ib in the second image IMG_b. The movement control unit 13 uses the position coordinates (xai, zai) of the inner eye corner Ia in the first image IMG_a, the position coordinates (xbi, zbi) of the inner eye corner Ib in the second image IMG_b, and the angel G (xg, zg) of the movable mirror 50 to calculate the distance D with a stereo image method. Further, the movement control unit 13 determines the focal position of the second imaging unit 40, based on the distance D, and generates the control information for moving the focus to the focal position. In other words, the movement control unit 13 uses the first imaging unit 30a and the second imaging unit 40 as stereo cameras, and adjusts the focus of the second imaging unit 40, which has narrow depth of field, to match with the eye position of the subject P.

Note that, in the example described above, the movement control unit 13 uses the position coordinates of the inner eye corners Ia and Ib, and may use position coordinates of outer eye corners Oa and Ob instead.

Figure 7:
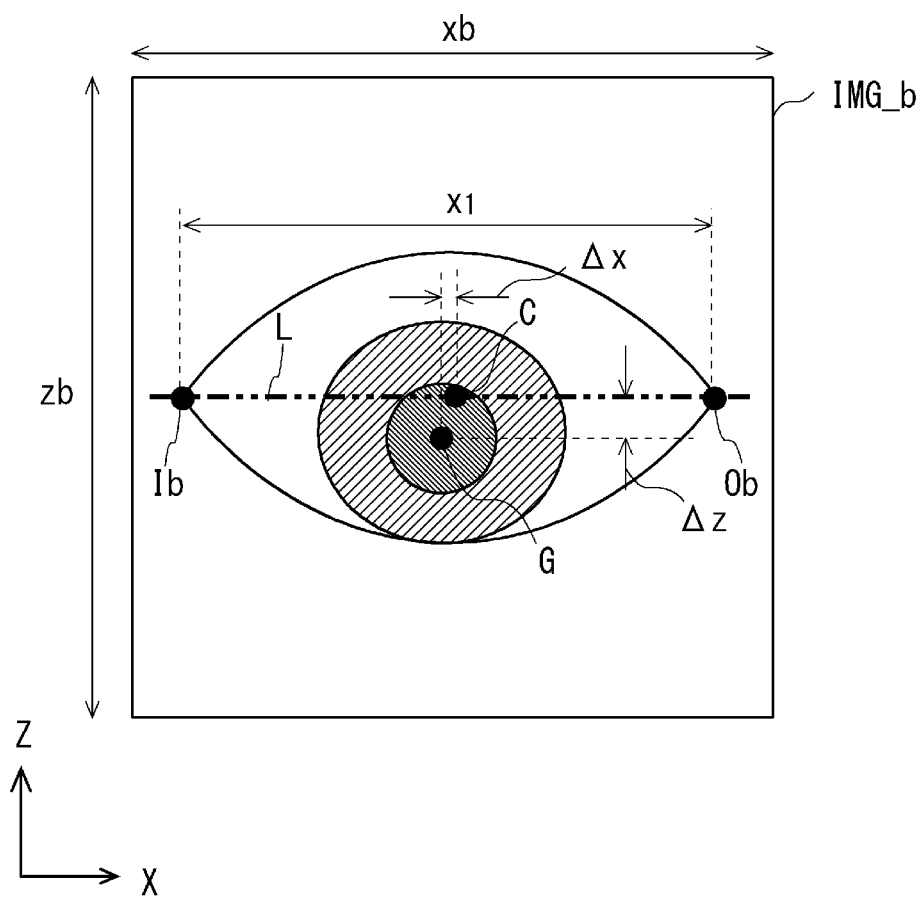
FIG. 7 is a diagram for describing state evaluation processing executed by a state evaluation unit according to the second example embodiment.

Next, with reference to FIG. 7, state evaluation processing is described in detail. FIG. 7 is a diagram for illustrating the state evaluation processing executed by the state evaluation unit 15 according to the second example embodiment. In this drawing, the second image IMG_b is also illustrated.

First, the state evaluation unit 15 calculates a relative position of a gravity center G of a pupil being a moving point with respect to a reference point in the second image IMG_b at each image-capturing timing. The reference point is preferably a fixed point at a position that is hardly changed by an opening degree of an eyelid or movement of a visual line. Herein, the state evaluation unit 15 may use a position of a cornea reflection image as the reference point, but uses a point based on a position being at least one of the outer eye corner Ob and the inner eye corner Ib in the second example embodiment. In other words, the state evaluation unit 15 calculates the relative position based on the position information relating to at least one of the outer eye corner Ob and the inner eye corner Ib and the position information relating to the gravity center G of the pupil. For example, the state evaluation unit 15 calculates the relative position between a linear line L connecting the position of the outer eye corner Ob and the position of the inner eye corner Ib to each other and the gravity center G of the pupil. The state evaluation unit 15 calculates distances Δx and Δz from the intermediate point between the outer eye corner Ob and the inner eye corner Ib (which may match with the center C of the second image IMG_b) to the gravity center G in the X-axis direction and the Z-axis direction, as the relative position of the gravity center G of the pupil. The state evaluation unit 15 may calculate a value acquired by standardizing the distances Δx and Δz in the X-axis direction and the Z-axis direction with the distance x1, as the relative position of the gravity center G of the pupil in the second image IMG_b. Note that the state evaluation unit 15 may only use the position of any one of the outer eye corner Ob and the inner eye corner Ib, as the reference point. Then, the state evaluation unit 15 evaluates the vibration state of the pupil, based on the difference information relating to the relative position of the gravity center G of the pupil between the adjacent image-capturing timings.

As described above, the state evaluation unit 15 uses the position of at least one of the outer eye corner Ob and the inner eye corner Ib, as the reference point. Therefore, as compared to a case of using a cornea reflection image, the system configuration is more simplified because the eye state measurement system 1a is not required to include an infrared light source for cornea reflection image formation. Further, the state evaluation unit 15 enables high speed processing and downsizing of the device because relative position calculation is facilitated and a calculation amount is reduced. Therefore, in the second example embodiment, description is made on a case in which the information processing device 10a is an independent computer device, but the information processing device 10a may be implemented in the first imaging unit 30a or the second imaging unit 40.

Figure 8:
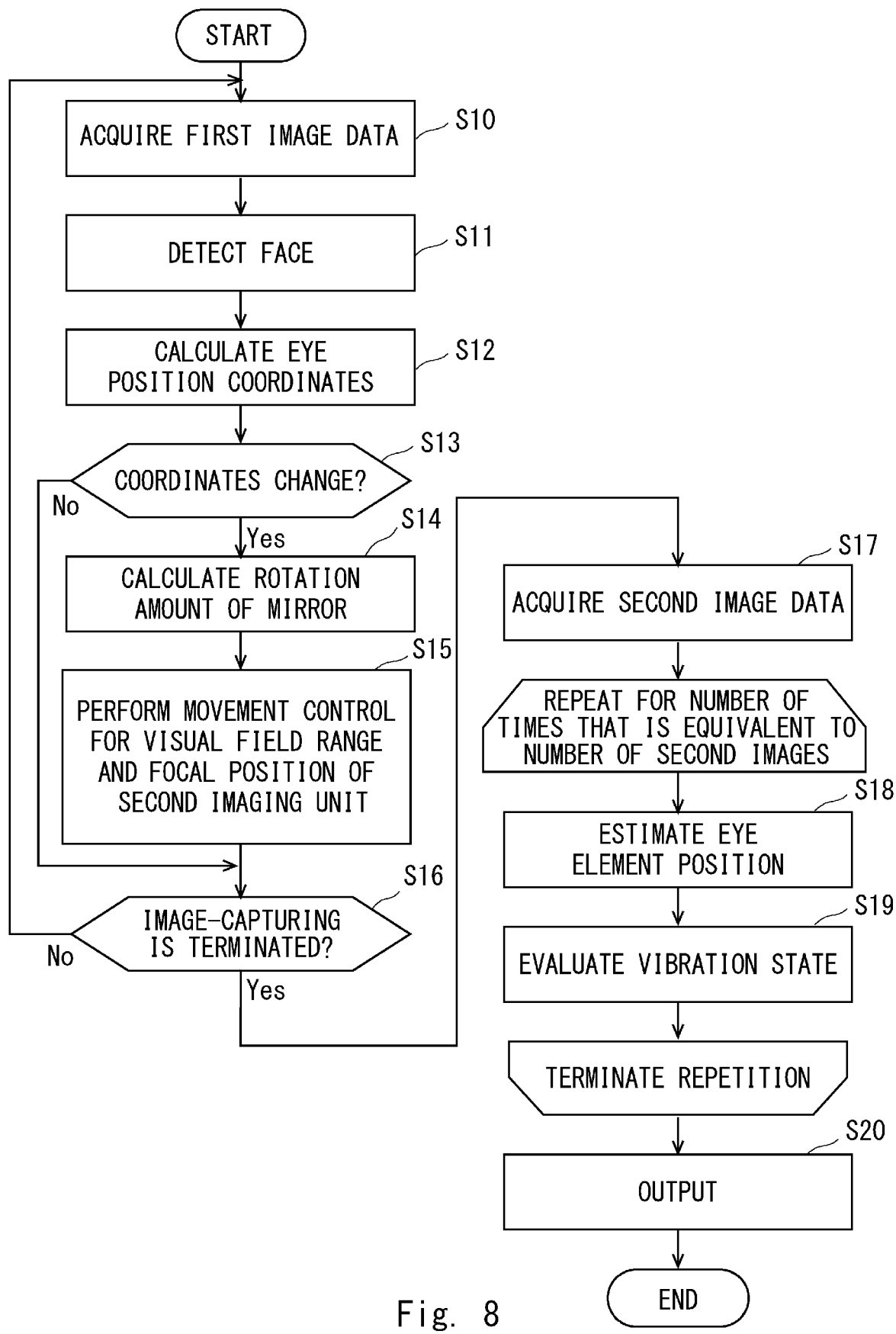
FIG. 8 is a flowchart illustrating a procedure of information processing of the information processing device according to the second example embodiment.

FIG. 8 is a flowchart illustrating a procedure of information processing executed by the information processing device 10a according to the second example embodiment.

First, the first acquisition unit 11 acquires the first image data at t=ti from the first imaging unit 30a at a predetermined frame rate (Step S10).

Subsequently, the movement control unit 13 detects the face of the subject P from the first image (Step S11). For example, the movement control unit 13 may detect the face of the subject P through use of a convolutional neural network (CNN) that is leant with the first image as an input. Then, the movement control unit 13 may generate a regularized image acquired by extracting an image region associated with the face of the subject P.

Subsequently, the movement control unit 13 calculates the eye position coordinates in the first image (Step S12). For example, the movement control unit 13 may detect the eye region of the subject P from the regularized image thus generated through template matching, and may calculate the position coordinates of the gravity center of the eye region in the first image, as the eye position coordinates.

Then, the movement control unit 13 determines whether the eye position coordinates in the first image at t=ti change as compared to the eye position coordinates in the first image at t=ti−1 (Step S13). When the eye position coordinates do not change (No in Step S13), the movement control unit 13 determines whether a series of image-capturing is terminated (Step S16), and the processing returns to Step S10 when a series of image-capturing is not terminated (No in Step S16). Meanwhile, when the eye position coordinates change (Yes in Step S13), the movement control unit 13 calculates the rotation amount of the movable mirror 50 at a subsequent image-capturing timing (for example, t=ti+1) with the above-mentioned method illustrated in FIG. 5 (Step S14). At this state, the movement control unit 13 may acquire the second image data from the second imaging unit 40 at the current or previous image-capturing timing (for example, the second image data at t=ti−1), and may calculate the rotation amount of the movable mirror 50, based on the eye position coordinates and the second image. Then, the movement control unit 13 generates the control signal for the visual field range in the X-axis direction and the Z-axis direction, based on the calculated rotation amount. Note that, in addition to this, the movement control unit 13 calculates the movement amount of the focal position of the second imaging unit 40 with the method illustrated in FIG. 6, and generates the control signal for the focal position, based on the movement amount.

Subsequently, the movement control unit 13 controls movement of the visual field range and the focal position of the second imaging unit 40 (Step S15). Specifically, the movement control unit 13 transmits, to the driving unit 51, the control signal for the visual field range in the X-axis direction and the Z-axis direction. Further, the movement control unit 13 transmits the control signal for the focal position to the liquid lens.

Subsequently, the movement control unit 13 determines whether a series of image-capturing is terminated (Step S16). When a series of image-capturing is not terminated (No in Step S16), the movement control unit 13 returns the processing to Step S10. When a series of image-capturing is terminated (Yes in Step S16), the processing proceeds to Step S17.

In Step S17, the second acquisition unit 12 acquires the second image data from the second imaging unit 40.

Herein, the information processing device 10a repeats the processing in Step S18 and Step S19 for the number of times that is equivalent to the number of frames of the second image.

In Step S18, the element position estimation unit 14 detects the eye region from the second image through, for example, template matching, and estimates position coordinates of the elements (the outer eye corner, the inner eye corner, and the gravity center of the pupil) of the eye. The element position estimation unit 14 may estimate the position coordinates of the gravity center of the pupil by detecting an image region of the pupil through, for example, binarization, edge detection, and Hough transformation, and calculating the position coordinates of the gravity center of the image region.

Then, in Step S19, the state evaluation unit 15 evaluates the vibration state by calculating the relative position of the gravity center of the pupil with the above-mentioned method illustrated in FIG. 7 and generating the difference information relating to the relative position.

Subsequently, in Step S20, the output unit 16 outputs the information relating to the evaluated vibration state.

Note that the processing in Step S17 to Step S19 may be executed in parallel to the processing in Step S10 to Step S16. Further, specific processing in each of the steps is not limited to the description given above.

As described above, the information processing device 10a according to the second example embodiment can exert effects similar to those in the first example embodiment. In particular, when microscopic vibration of an eyeball is to be measured, vibration of a head needs to be strictly suppressed, and hence the head needs to be firmly fixed. Therefore, it is difficult to fix a head immediately after a subject have the head operated due to a brain disease, and thus an eye state such as a saccade phenomenon cannot be examined. Further, the current technology only enables examination on a response of a brain in a tensed state due to fixation of a head. The same holds true for determination on a degree of interest in an image when a subject sees the image, as well as examination on a recovery state from a brain disease.

However, with the information processing system 10a according to the second example embodiment, such a problem can be solved. With this, for example, an evaluation value acquired from the information processing system 10a through evaluation can be utilized as evidence for deciding a transitional phase of rehabilitation from a brain disease, and a medical worker can easily diagnose a state of recovery from illness while alleviating a burden on a subject being a patient. Further, an evaluation value acquired from the information processing system 10a through evaluation is collected as a degree of interest of a subject being a consumer in an advertisement image, and thus a company can measure an effect of the advertisement quantitatively.

Third Example Embodiment

Figure 9:
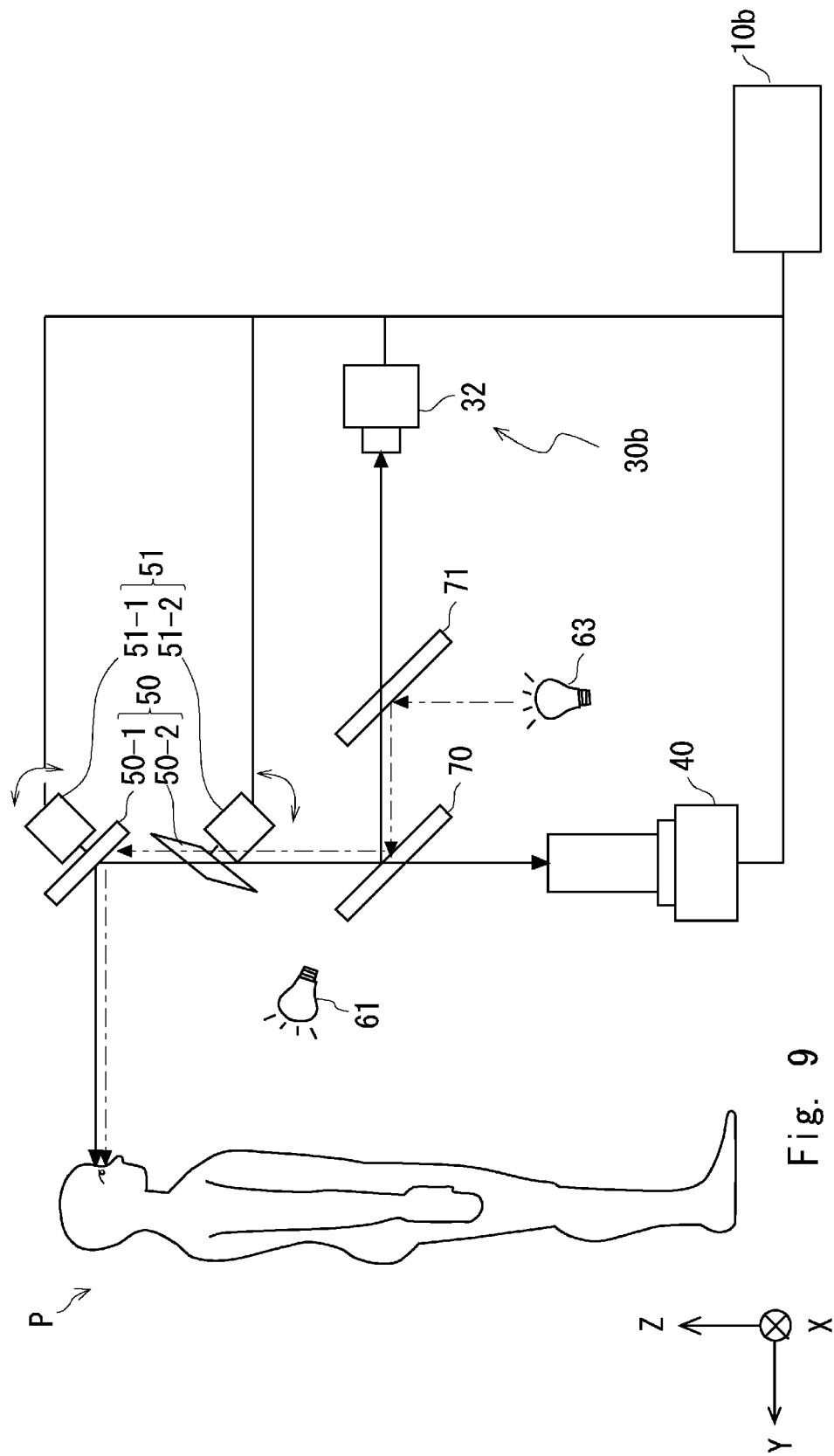
FIG. 9 is a system configuration diagram of an eye state measurement system according to a third example embodiment.

Next, with reference to FIG. 9, a third example embodiment of the present disclosure is described. The third example embodiment is characterized in that the visual field range of the first imaging unit moves according to movement of the head of the subject and the visual field range of the second imaging unit also moves accordingly.

FIG. 9 is a system configuration diagram of an eye state measurement system 1b according to the third example embodiment.

The eye state measurement system 1b according to the third example embodiment basically includes configurations and functions that are similar to those of the eye state measurement system 1a according to the second example embodiment. However, the eye state measurement system 1b is different from the eye state measurement system 1a in that a first imaging unit 30b and an information processing device 10b are included in place of the first imaging unit and the information processing device 10a, and a light source 63, a long-pass filter 70, and a half mirror 71 are further included.

The first imaging unit 30b includes a tracking camera 32 that has a visual field range moving according to movement of the head of the subject P. In the third example embodiment, the visual field range of the tracking camera 32 moves according to movement of the eye region of the subject P in such a way that the eye region of the subject P is captured at the center of the first image. Specifically, similarly to the second imaging unit 40, the visual field range of the tracking camera 32 moves by rotation of the movable mirror 50 by the driving unit 51 following the control signal for the visual field range of the information processing device 10b. In other words, the movable mirror 50 moves an optical axis of the first imaging unit 30b in addition to the optical axis of the second imaging unit 40. As a result, the visual field range of the second imaging unit moves in association with movement of the visual field range of the tracking camera 32. Herein, a detection wavelength of a photodetector of the tracking camera 32 is referred to as a wavelength for tracking, and the wavelength for tracking is smaller than the wavelength for pupil detection being the detection wavelength of the photodetector of the second imaging unit 40. As an example, the wavelength for tracking is 850 [nm]. Note that the angle of view, the focal distance, and the frame rate of the tracking camera 32 are similar to those of the wide-angle camera 31 in the second example embodiment.

The light source 63 is a light source that irradiates the eye region of the subject P. The light source 63 is a light source having a wavelength region associated with the wavelength for tracking, and is a near-infrared light source of 850 [nm] in the third example embodiment.

The half mirror 71 is a half mirror that reflects part of 850-nm incident light from the light source 63 toward the long-pass filter 70. Further, the half mirror 71 causes part of 850-nm incident light from the long-pass filter 70 to pass therethrough toward the tracking camera 32. Note that the half mirror 71 may be a beam splitter having a freely selected ratio of transmission and reflection, in place of a half mirror.

The long-pass filter 70 is an optical filter that causes light having the wavelength for pupil detection to pass therethrough and reflects light having the wavelength for tracking. The long-pass filter 70 is provided between the second imaging unit 40 and the movable mirror 50, and causes incident light having the wavelength for pupil detection from the movable mirror 50 to pass therethrough toward the second imaging unit 40. Further, the long-pass filter 70 reflects, toward the half mirror 71, incident light having the wavelength for tracking from the movable mirror 50.

In other words, part of light from the light source 63 arrives at the eye region of the subject P via a path including the half mirror 71, the long-pass filter the second movable mirror 50-2, and the first movable mirror 50-1 in the stated order.

Further, the tracking camera 32 of the first imaging unit 30b captures an image of the eye region (or the face) of the subject P at the first angle of view with incident light through a path including the eye region (or the face) of the subject P, the first movable mirror 50-1, the second movable mirror 50-2, the long-pass filter 70, the half mirror 71, and the tracking camera 32 in the stated order.

Further, the second imaging unit 40 captures an image of the eye region of the subject P at the second angle of view with incident light through a path including the eye region of the subject P, the first movable mirror 50-1, the second movable mirror 50-2, the long-pass filter 70, and the second imaging unit 40 in the stated order.

The information processing device 10b basically includes configurations and functions that are similar to those of the information processing device 10a, but is different from the second example embodiment in movement control processing executed by the movement control unit 13 in the X-axis direction and the Z-axis direction (processing shown in Step S14 in FIG. 5 and FIG. 8).

In the third example embodiment, first, the movement control unit 13 calculates the eye position coordinates in the first image. Then, the movement control unit 13 calculates the rotation amounts of the first movable mirror 50-1 and the second movable mirror 50-2 in such a way that the gravity center of the eye region in the first image is arranged at the center of the first image at a subsequent image-capturing timing. Herein, the tracking camera 32 of the first imaging unit 30b has the frame rate equal to or greater than the frame rate of the second imaging unit 40, and hence the eye region of the subject P is also captured at the image center of the second image captured by the second imaging unit 40.

As described above, according to the third example embodiment, the information processing device 10b is capable of moving the visual field range of the second imaging unit 40 following movement of the head of the subject P at higher accuracy. With this, the information processing device 10b can suitably evaluate a change of a state of the eye of the subject P while the head is in a relaxed posture without being fixed.

Fourth Example Embodiment

Figure 10:
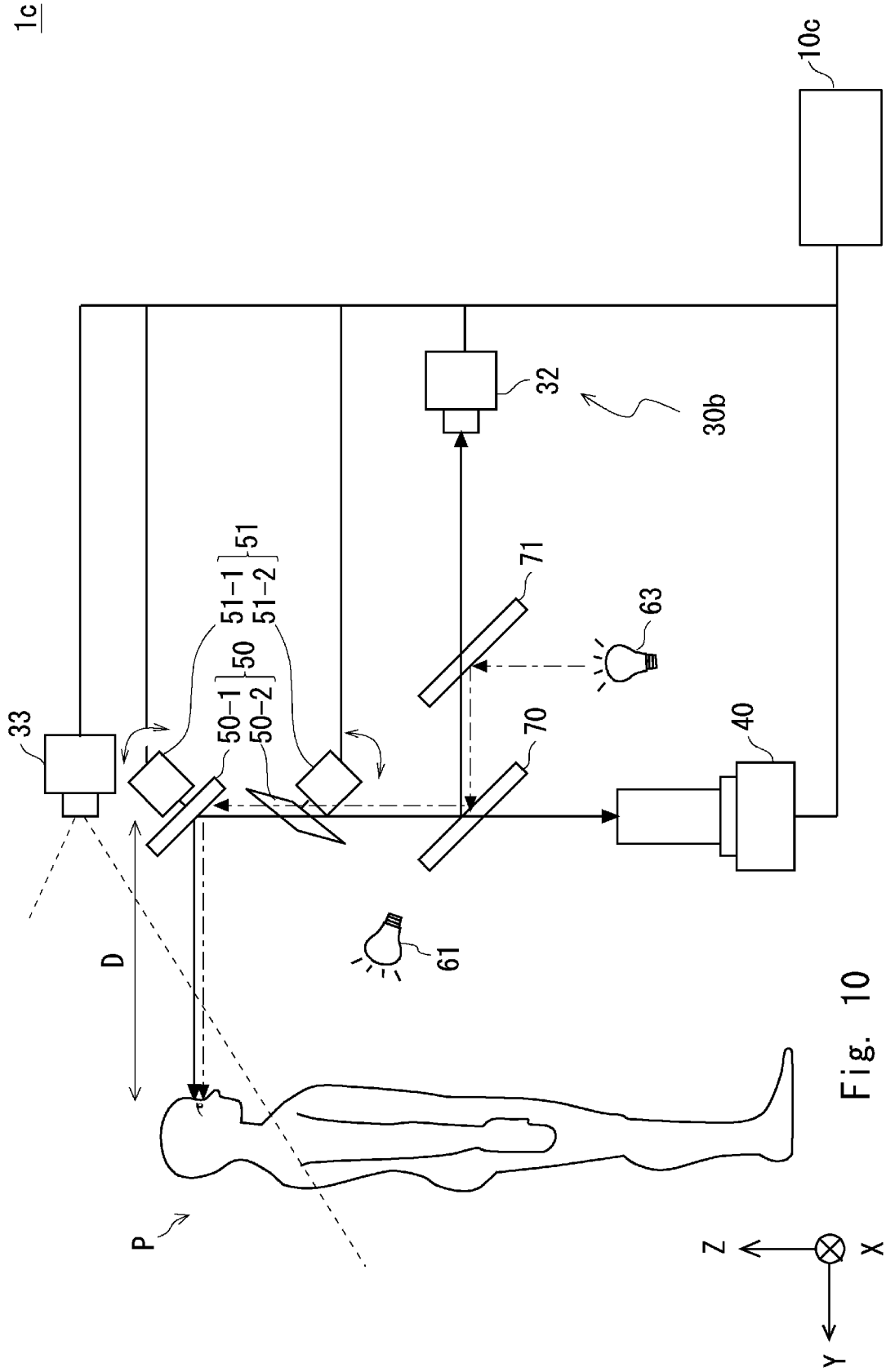
FIG. 10 is a system configuration diagram of an eye state measurement system according to a fourth example embodiment.

Next, with reference to FIG. 10 and FIG. 11, a fourth example embodiment of the present disclosure is described. The fourth example embodiment is characterized in that a position of a visual field range of a narrowest-angle camera is roughly adjusted with a widest-angle image and a position of a visual field range is finely adjusted with an intermediate-angle image.

FIG. 10 is a system configuration diagram of an eye state measurement system 1c according to the fourth example embodiment. The eye state measurement system 1c according to the fourth example embodiment basically includes configurations and functions that are similar to those of the eye state measurement system 1b according to the third example embodiment. However, the eye state measurement system 1c is different from the eye state measurement system 1b in that a third imaging unit 33 and an information processing device 10c in place of the information processing device 10b are included.

The third imaging unit 33 is a camera that captures an image of at least the head of the subject P at a third angle of view and generates third image data relating to a third image. The third angle of view is larger than the first angle of view of the tracking camera 32, and is larger than the second angle of view of the second imaging unit 40. When the third image data is generated, the third imaging unit 33 transmits the third image data to the information processing device 10c.

The information processing device 10c basically includes functions that are similar to those of the information processing device 10b, but is different from the information processing device 10b in that movement control for the visual field ranges of the tracking camera 32 and the second imaging unit 40 is roughly adjusted based on the third image data.

FIG. 11 is a block diagram illustrating a functional configuration of the information processing device 10c according to the fourth example embodiment. In addition to the configuration of the information processing device 10b, the information processing device 10c includes a third acquisition unit 17. The third acquisition unit 17 receives and acquires the third image data from the third imaging unit 33, and supplies the third image data to the movement control unit 13.

The movement control unit 13 detects the face of the subject P from the third image, calculates the eye position coordinates in the third image, and calculates the rotation amount of the movable mirror 50, based on the eye position coordinates, in such a way that the eye region falls within the first image. Then, the movement control unit 13 transmits, to the driving unit 51, the control signal of the visual field range based on the rotation amount, and roughly adjusts the inclination angle of the movable mirror 50.

Such rough adjustment processing may be executed before Step S10 in FIG. 8. Further, for preventing an increase of a processing time, the rough adjustment processing may be executed only when the face of the subject P is not detected from the first image in Step S11 in FIG. 8 or when the eye region of the subject P is not detected from the first image in Step S12, for example.

Note that the movement control processing in which the first image at the first angle of view narrower than the third image is used is processing associated with Step S10 to Step S15 in FIG. 8, but may also be referred to fine adjustment processing. The first angle of view in the fourth example embodiment is only required to be an angle of view for capturing an image of at least the eye region of the subject P, and may be narrower than the first angle of view in the second example embodiment and the third example embodiment. In this case, in the fine adjustment processing, face detection processing associated with Step S11 in FIG. 8 may be omitted. With this, even when the rough adjustment processing is added, an increase of a time for a series of processing can be prevented.

As described above, even when the head of the subject P largely moves, the information processing device 10c according to the fourth example embodiment is capable of moving the visual field range of the second imaging unit 40 in such a way as to prevent the eye region of the subject P from deviating from the visual field range of the second imaging unit 40. With this, the subject P can freely move during image-capturing, and hence the information processing device 10c is capable of evaluating a change in state of an eye in a more relaxed state.

With reference to the example embodiments, the present disclosure is described above, but the invention of the present application is not limited thereto. Various modifications that can be understood by a person skilled in the art may be made to the configurations and the details of the invention of the present application within the scope of the invention. For example, the state of the eye being an evaluation target is a contraction amount of the pupil, and the state evaluation unit 15 may evaluate a contraction amount of the pupil of the subject P, based on the chronological data relating to the second image. Further, when an image such as an advertisement image is viewed, the state evaluation unit may evaluate a degree of interest, based on a contraction amount of the pupil.

In the example embodiment described above, the present disclosure is described as a hardware configuration, but the present disclosure is not limited thereto. In the present disclosure, various processing relating to the state evaluation method can be executed by causing a processor to execute a computer processing.

In the example described above, a program can be stored through use of a non-transitory computer readable medium of various types, and can be supplied to a computer. The non-transitory computer readable medium includes a tangible storage medium of various types. Examples of the non-transitory computer readable medium include a magnetic recording medium (for example, a flexible disk, a magnetic tape, a hard disk drive), a magneto-optic recording medium (for example, a magneto-optic disk), a CD-read only memory (ROM), CD-R, CD-R/W, and a semiconductor memory (for example, a mask ROM, a programmable ROM (PROM), an erasable PROM (EPROM), a flash ROM, a random access memory (RAM)). Further, the program may be supplied to the computer from a transitory computer readable medium of various types. Examples of the transitory computer readable medium include an electric signal, an optical signal, and an electromagnetic wave. The transitory computer readable medium is capable of supplying the program to the computer via a wired communication path such as an electric cable and an optical fiber or via a wireless communication path.

In the example embodiments described above, the computer is configured as a computer system including a personal computer, a word processor, or the like. However, the computer may be configured as, but not limited to, a server of a local area network (LAN), a host of a computer (personal computer) communication, a computer system connected to the Internet, or the like. Further, the computer may be configured as a network as whole by functionally distributing devices via the network.

A part or the entirety of the example embodiments described above may be described as in the following supplementary notes, but is not limited to the followings.

(Supplementary Note 1)

An information processing system including:
a first acquisition unit configured to acquire, from a first imaging unit, image data relating to a first image of a head of a subject, the first image being captured at a first angle of view;
a second acquisition unit configured to acquire, from a second imaging unit, image data relating to a second image of an eye region of the subject, the second image being captured at a second angle of view narrower than the first angle of view;
a movement control unit configured to move a visual field range of the second imaging unit, based on position information relating to the head of the subject, the position information being acquired based on the first image; and
a state evaluation unit configured to evaluate a change in state of an eye of the subject, based on chronological data relating to the second image.

(Supplementary Note 2)

The information processing system according to Supplementary Note 1, wherein
the movement control unit generates change information relating to a position of the head of the subject, based on chronological data relating to the first image, and moves the visual field range of the second imaging unit, based on the change information.

(Supplementary Note 3)

The information processing system according to Supplementary Note 2, wherein
the first acquisition unit acquires image data relating to the first image at a frame rate equal to or greater than a frame rate at which the second acquisition unit acquires image data relating to the second image.

(Supplementary Note 4)

The information processing system according to any one of Supplementary Notes 1 to 3, further including:
an element position estimation unit configured to estimate a position of a gravity center of a pupil of the subject and a position of at least one of an outer eye corner and an inner eye corner in the second image, wherein
the state evaluation unit evaluates a vibration state of the pupil of the subject, based on position information relating to at least one of the outer eye corner and the inner eye corner and position information relating to the gravity center of the pupil.

(Supplementary Note 5)

The information processing system according to Supplementary Note 4, wherein
the state evaluation unit calculates a relative position of the gravity center of the pupil with respect to a linear line connecting a position of the outer eye corner and a position of the inner eye corner, and evaluates a vibration state of the pupil of the subject, based on the relative position.

(Supplementary Note 6)

The information processing system according to any one of Supplementary Notes 1 to 3, wherein
the state evaluation unit evaluates a contraction amount of the pupil of the subject, based on the chronological data relating to the second image.

(Supplementary Note 7)

An eye state measurement system including:
a first imaging unit configured to capture an image of a head of a subject at a first angle of view;
a second imaging unit configured to capture an image of an eye region of the subject at a second angle of view narrower than the first angle of view; and
an information processing device, wherein
the information processing device includes:
a first acquisition unit configured to acquire, from the first imaging unit, image data relating to a first image;
a second acquisition unit configured to acquire, from the second imaging unit, image data relating to a second image;
a movement control unit configured to move a visual field range of the second imaging unit, based on position information relating to the head of the subject, the position information being acquired based on the first image; and
a state evaluation unit configured to evaluate a change in state of an eye of the subject, based on chronological data relating to the second image.

(Supplementary Note 8)

The eye state measurement system according to Supplementary Note 7, further including:
a movable mirror configured to move an optical axis of the second imaging unit; and
a driving unit configured to drive the movable mirror, wherein
the movement control unit generates change information relating to a position of the head of the subject, based on chronological data relating to the first image, and calculates a rotation amount of the movable mirror, based on the change information.

(Supplementary Note 9)

The eye state measurement system according to Supplementary Note 8, wherein
the movable mirror move optical axes of the first imaging unit and the second imaging unit.

(Supplementary Note 10)

The eye state measurement system according to any one of Supplementary Notes 7 to 9, wherein
the first imaging unit captures an image of an object at a frame rate equal to or greater than a frame rate of the second imaging unit.

(Supplementary Note 11)

An information processing method including:
acquiring, from a first imaging unit, image data relating to a first image of a head of a subject, the first image being captured at a first angle of view;
acquiring, from a second imaging unit, image data relating to a second image of an eye region of the subject, the second image being captured at a second angle of view narrower than the first angle of view;
moving a visual field range of the second imaging unit, based on position information relating to the head of the subject, the position information being acquired based on the first image; and evaluating a change in state of an eye of the subject, based on chronological data relating to the second image.

(Supplementary Note 12)

A program for causing a computer to execute:

first acquisition processing of acquiring, from a first imaging unit, image data relating to a first image of a head of a subject, the first image being captured at a first angle of view;

second acquisition processing of acquiring, from a second imaging unit, image data relating to a second image of an eye region of the subject, the second image being captured at a second angle of view narrower than the first angle of view;

movement control processing of moving a visual field range of the second imaging unit, based on position information relating to the head of the subject, the position information being acquired based on the first image; and state evaluation processing of evaluating a change in state of an eye of the subject, based on chronological data relating to the second image.

This application is based upon and claims the benefit of priority from Japanese patent application No. 2020-176066, filed on Oct. 20, 2020, the disclosure of which is incorporated herein in its entirety by reference.

INDUSTRIAL APPLICABILITY

The information processing system according to the present disclosure is applicable for evaluating a change in state of an eye of a subject.

REFERENCE SIGNS LIST 1a, 1b, 1c EYE STATE MEASUREMENT SYSTEM
10, 10a, 10b, 10c INFORMATION PROCESSING SYSTEM (INFORMATION PROCESSING DEVICE)
11 FIRST ACQUISITION UNIT
12 SECOND ACQUISITION UNIT
13 MOVEMENT CONTROL UNIT
14 ELEMENT POSITION ESTIMATION UNIT
15 STATE EVALUATION UNIT
16 OUTPUT UNIT
17 THIRD ACQUISITION UNIT
30a, 30b FIRST IMAGING UNIT
31 WIDE-ANGLE CAMERA
32 TRACKING CAMERA
33 THIRD IMAGING UNIT
40 SECOND IMAGING UNIT
50 MOVABLE MIRROR
51 DRIVING UNIT
61 LIGHT SOURCE
63 LIGHT SOURCE
70 LONG-PASS FILTER
71 HALF MIRROR
100 PROCESSOR
101 ROM
102 RAM
103 INTERFACE (IF) UNIT
P SUBJECT
IMG_a FIRST IMAGE
IMG_b SECOND IMAGE

The invention claimed is:

1. An information processing system comprising:
at least one memory storing instructions, and
at least one processor configured to execute the instructions to:
acquire, from first photodetector, image data relating to a first image of a head of a subject, the first image being captured at a first angle of view;
acquire, from second photodetector, image data relating to a second image of an eye region of the subject, the second image being captured at a second angle of view narrower than the first angle of view;
move a visual field range of the second photodetector, based on position information relating to the head of the subject, the position information being acquired based on the first image; and
evaluate a change in state of an eye of the subject, based on chronological data relating to the second image,
wherein the at least one processor is configured to execute the instructions to acquire image data relating to the first image at a frame rate equal to or greater than a frame rate at which the at least one processor is configured to execute the instructions to acquire image data relating to the second image,
wherein the frame rate of the first photodetector is 120 fps to 1,200 fps and
wherein the frame rate of the second photodetector is 120 fps to 1,000 fps.

2. The information processing system according to claim 1, wherein the at least one processor is configured to generate change information relating to a position of the head of the subject, based on chronological data relating to the first image, and move a visual field range of the second photodetector, based on the change information.

3. The information processing system according to claim 1, wherein the at least one processor is configured to estimate a position of a gravity center of a pupil of the subject and a position of at least one of an outer eye corner and an inner eye corner in the second image,
wherein the at least one processor is configured to evaluate a vibration state of the pupil of the subject, based on position information relating to at least one of the outer eye corner and the inner eye corner and position information relating to the gravity center of the pupil.

4. The information processing system according to claim 3, wherein the at least one processor is configured to calculate a relative position of the gravity center of the pupil with respect to a linear line connecting a position of the outer eye corner and a position of the inner eye corner, and evaluate a vibration state of the pupil of the subject, based on the relative position.

5. The information processing system according to claim 1, wherein the at least one processor is configured to evaluate a contraction amount of a pupil of the subject, based on chronological data relating to the second image.

6. An eye state measurement system comprising:
a first photodetector for capturing an image of a head of a subject at a first angle of view;
a second photodetector for capturing an image of an eye region of the subject at a second angle of view narrower than the first angle of view; and
an information processing device,
wherein the information processing device comprises:
at least one memory storing instructions, and
at least one processor configured to execute the instructions to;

acquire from the first photodetector, image data relating to a first image;

acquire from the second photodetector, image data relating to a second image;

move a visual field range of the second photodetector, based on position information relating to the head of the subject, the position information being acquired based on the first image; and evaluate a change in state of an eye of the subject, based on chronological data relating to the second image, wherein the first photodetector captures an image of an object at a frame rate equal to or greater than a frame rate of the second photodetector, wherein the frame rate of the first photodetector is 120 fps to 1,200 fps and wherein the frame rate of the second photodetector is 120 fps to 1,000 fps.

7. The eye state measurement system according to claim 6, further comprising:

a movable mirror configured to move an optical axis of the second photodetector; and a driver configured to rotate the movable mirror, wherein the at least one processor is configured to generate change information relating to a position of the head of the subject, based on chronological data relating to the first image, and calculate a rotation amount of the movable mirror, based on the change information.

8. The eye state measurement system according to claim 7, wherein the movable mirror moves optical axes of the first photodetector and the second photodetector.

9. An information processing method comprising:

acquiring, from a first photodetector, image data relating to a first image of a head of a subject, the first image being captured at a first angle of view;

acquiring, from a second photodetector, image data relating to a second image of an eye region of the subject, the second image being captured at a second angle of view narrower than the first angle of view;

moving a visual field range of the second photodetector, based on position information relating to the head of the subject, the position information being acquired based on the first image; and evaluating a change in state of an eye of the subject, based on chronological data relating to the second image, wherein the first photodetector captures an image of an object at a frame rate equal to or greater than a frame rate of the second photodetector, wherein the frame rate of the first photodetector is 120 fps to 1,200 fps and wherein the frame rate of the second photodetector is 120 fps to 1,000 fps.

10. Non-transitory computer readable medium configured to store a program for causing a computer to execute the method according to claim 9.

* * * * *